United States Patent
Ma et al.

(10) Patent No.: US 12,280,232 B2
(45) Date of Patent: *Apr. 22, 2025

(54) IV ACCESS PORT CAP FOR PROVIDING ANTIMICROBIAL PROTECTION

(71) Applicant: Becton, Dickinson and Company, Franklin Lakes, NJ (US)

(72) Inventors: Yiping Ma, Layton, UT (US); Siddarth Kamath Shevgoor, Singapore (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/227,211

(22) Filed: Jul. 27, 2023

(65) Prior Publication Data

US 2023/0364407 A1    Nov. 16, 2023

Related U.S. Application Data

(63) Continuation of application No. 17/374,729, filed on Jul. 13, 2021, now Pat. No. 11,752,319, which is a
(Continued)

(51) Int. Cl.
*A61M 39/16* (2006.01)
*A61M 25/00* (2006.01)
(Continued)

(52) U.S. Cl.
CPC ...... *A61M 39/162* (2013.01); *A61M 25/0017* (2013.01); *A61M 39/20* (2013.01);
(Continued)

(58) Field of Classification Search
CPC ............... A61M 39/162; A61M 39/20; A61M 39/0208; A61M 39/165; A61M 25/0017; A61M 2025/0056
See application file for complete search history.

(56) References Cited

U.S. PATENT DOCUMENTS 2,961,682 A    11/1960   Wurmbock et al.
3,863,632 A    2/1975    Schwartz
(Continued)

FOREIGN PATENT DOCUMENTS

CN    101077433 A    11/2007
CN    101316621 A    12/2008
(Continued)

OTHER PUBLICATIONS

Corrected Petition for Inter Partes Review Under 35 U.S.C . . . sctn . . . sctn. 311-319 and 37 C.F.R. .sctn. 42,100 et seq., USPTO, Patent Trial and Appeal Board, *Excelsior Medical Corporation* v. *Becton, Dickinson and Company*, Case PR2014-00880, U.S. Pat. No. 8,740,864, pp. 1-48, Jun. 23, 2014.
(Continued)

*Primary Examiner* — Joel M Attey
*Assistant Examiner* — John A Doubrava
(74) *Attorney, Agent, or Firm* — Kirton McConkie; Whitney Blair; Christopher DiLeo

(57) ABSTRACT

A cap is configured to provide antimicrobial protection to a female luer port of an intravenous device. The cap distributes an antimicrobial solution within the intraluminal surfaces of the port when the cap is connected to the port. A cap may also be designed to distribute an antimicrobial solution around the exterior surfaces of the port. Once connected to a port, the cap can form a seal that minimizes the evaporation of the antimicrobial solution from within the lumen of a port. The cap can therefore provide antimicrobial protection against another device that is connected to the port once the cap is removed.

16 Claims, 17 Drawing Sheets

Related U.S. Application Data continuation of application No. 16/109,376, filed on Aug. 22, 2018, now Pat. No. 11,090,477, which is a continuation of application No. 15/674,389, filed on Aug. 10, 2017, now Pat. No. 10,124,157, which is a continuation of application No. 15/041,931, filed on Feb. 11, 2016, now Pat. No. 9,750,929, which is a continuation of application No. 14/185,827, filed on Feb. 20, 2014, now Pat. No. 9,283,369.

(51) Int. Cl.
    *A61M 39/20*     (2006.01)
    *A61M 39/02*     (2006.01)

(52) U.S. Cl.
    CPC . *A61M 2025/0056* (2013.01); *A61M 39/0208* (2013.01); *A61M 39/165* (2013.01)

(56) References Cited

U.S. PATENT DOCUMENTS

| | | | |
|---|---|---|---|
| 4,280,632 A | 7/1981 | Yuhara | |
| 4,282,891 A | 8/1981 | Duceppe | |
| 4,324,239 A * | 4/1982 | Gordon | A61M 39/26 604/122 |
| 4,354,490 A | 10/1982 | Rogers | |
| 4,417,890 A | 11/1983 | Dennehey et al. | |
| 4,432,764 A | 2/1984 | Lopez | |
| 4,440,207 A | 4/1984 | Genatempo et al. | |
| 4,444,310 A | 4/1984 | Odell | |
| 4,531,937 A | 7/1985 | Yates | |
| 4,584,192 A | 4/1986 | Dell et al. | |
| 4,624,664 A | 11/1986 | Peluso et al. | |
| 4,655,762 A | 4/1987 | Rogers | |
| 4,671,306 A | 6/1987 | Spector | |
| 4,716,032 A | 12/1987 | Westfall et al. | |
| 4,753,358 A | 6/1988 | Virca et al. | |
| 4,778,447 A | 10/1988 | Velde et al. | |
| 4,915,934 A | 4/1990 | Tomlinson | |
| 4,925,668 A | 5/1990 | Khan et al. | |
| 4,989,733 A | 2/1991 | Patry | |
| 4,991,629 A | 2/1991 | Ernesto et al. | |
| 5,023,082 A | 6/1991 | Friedman et al. | |
| 5,195,957 A | 3/1993 | Tollini | |
| 5,242,425 A | 9/1993 | White et al. | |
| 5,334,388 A | 8/1994 | Hoang et al. | |
| 5,335,373 A | 8/1994 | Dangman et al. | |
| 5,507,728 A | 4/1996 | Erskine | |
| 5,507,733 A | 4/1996 | Larkin et al. | |
| 5,512,199 A | 4/1996 | Khan et al. | |
| 5,547,662 A | 8/1996 | Khan et al. | |
| 5,554,106 A | 9/1996 | Layman-Spillar et al. | |
| 5,569,207 A | 10/1996 | Gisselberg et al. | |
| 5,616,338 A | 4/1997 | Fox, Jr. et al. | |
| 5,620,424 A | 4/1997 | Abramson | |
| 5,639,310 A | 6/1997 | Giampaolo, Jr. | |
| 5,641,464 A | 6/1997 | Briggs, III et al. | |
| 5,686,096 A | 11/1997 | Khan et al. | |
| 5,694,978 A | 12/1997 | Heilmann et al. | |
| 5,695,474 A | 12/1997 | Daugherty | |
| 5,702,017 A | 12/1997 | Goncalves | |
| 5,722,537 A | 3/1998 | Sigler | |
| 5,743,884 A | 4/1998 | Hasson et al. | |
| 5,861,440 A | 1/1999 | Gohla et al. | |
| 5,954,957 A | 9/1999 | Chin-Loy et al. | |
| 5,989,229 A | 11/1999 | Chiappetta | |
| 6,051,609 A | 4/2000 | Yu et al. | |
| 6,116,468 A | 9/2000 | Nilson | |
| 6,117,114 A | 9/2000 | Paradis | |
| 6,196,998 B1 | 3/2001 | Jansen et al. | |
| 6,213,978 B1 | 4/2001 | Voyten | |
| 6,227,391 B1 | 5/2001 | King | |
| 6,337,357 B1 | 1/2002 | Fukunishi et al. | |
| 6,413,539 B1 | 7/2002 | Shalaby | |
| 6,488,942 B1 | 12/2002 | Ingemann | |
| 6,523,686 B1 | 2/2003 | Bae | |
| RE38,145 E | 6/2003 | Lynn | |
| 6,708,363 B2 | 3/2004 | Larsen | |
| 6,846,846 B2 | 1/2005 | Modak et al. | |
| 6,861,060 B1 | 3/2005 | Luriya et al. | |
| 6,911,025 B2 | 6/2005 | Miyahara | |
| 6,994,315 B2 | 2/2006 | Ryan et al. | |
| 7,083,605 B2 | 8/2006 | Miyahara | |
| 7,198,800 B1 | 4/2007 | Ko | |
| 7,268,165 B2 | 9/2007 | Greten et al. | |
| 7,682,561 B2 | 3/2010 | Davis et al. | |
| 7,704,935 B1 | 4/2010 | Davis et al. | |
| 7,828,186 B2 | 11/2010 | Wales | |
| 7,922,701 B2 | 4/2011 | Buchman | |
| 8,065,773 B2 | 11/2011 | Vaillancourt et al. | |
| 8,113,731 B2 | 2/2012 | Cable, Jr. et al. | |
| 9,039,989 B2 | 5/2015 | Liu et al. | |
| 9,283,369 B2 | 3/2016 | Ma et al. | |
| 9,399,125 B2 | 7/2016 | Burkholz | |
| 9,480,833 B2 | 11/2016 | Hoang et al. | |
| 9,545,495 B2 | 1/2017 | Goral et al. | |
| 9,895,524 B2 | 2/2018 | Lareau | |
| 2001/0016589 A1 | 8/2001 | Modak et al. | |
| 2001/0053895 A1 | 12/2001 | Vaillancourt | |
| 2002/0045643 A1 | 4/2002 | Muller et al. | |
| 2002/0045843 A1 | 4/2002 | Barker et al. | |
| 2002/0144705 A1 | 10/2002 | Brattesani et al. | |
| 2002/0177814 A1 | 11/2002 | Meng et al. | |
| 2002/0193752 A1 | 12/2002 | Lynn | |
| 2003/0072781 A1 | 4/2003 | Pelerin | |
| 2003/0109853 A1 | 6/2003 | Harding et al. | |
| 2003/0153865 A1 | 8/2003 | Connell et al. | |
| 2003/0162839 A1 | 8/2003 | Symington et al. | |
| 2004/0004019 A1 | 1/2004 | Busch | |
| 2004/0039349 A1 | 2/2004 | Modak et al. | |
| 2004/0258560 A1 | 12/2004 | Lake, Jr. et al. | |
| 2005/0124970 A1 | 6/2005 | Kunin et al. | |
| 2005/0147524 A1 | 7/2005 | Bousquet | |
| 2005/0147525 A1 | 7/2005 | Bousquet | |
| 2005/0222542 A1 | 10/2005 | Burkholz et al. | |
| 2006/0015086 A1 | 1/2006 | Rasmussen et al. | |
| 2006/0030827 A1 | 2/2006 | Raulerson et al. | |
| 2006/0135962 A1 | 6/2006 | Kick et al. | |
| 2006/0165751 A1 | 7/2006 | Chudzik et al. | |
| 2006/0239954 A1 | 10/2006 | Sancho | |
| 2007/0112333 A1 | 5/2007 | Hoang et al. | |
| 2007/0202177 A1 | 8/2007 | Hoang | |
| 2007/0225648 A1 | 9/2007 | Winsor et al. | |
| 2007/0225660 A1 | 9/2007 | Lynn | |
| 2007/0282280 A1 | 12/2007 | Tennican | |
| 2008/0019889 A1 | 1/2008 | Rogers et al. | |
| 2008/0027399 A1 | 1/2008 | Harding et al. | |
| 2008/0033371 A1 | 2/2008 | Updegraff et al. | |
| 2008/0075761 A1 | 3/2008 | Modak et al. | |
| 2008/0086091 A1 | 4/2008 | Anderson et al. | |
| 2008/0147047 A1 | 6/2008 | Davis et al. | |
| 2008/0177250 A1 | 7/2008 | Howlett et al. | |
| 2008/0182921 A1 | 7/2008 | Suh et al. | |
| 2009/0008393 A1 | 1/2009 | Howlett et al. | |
| 2009/0028750 A1 | 1/2009 | Ryan | |
| 2009/0028756 A1 | 1/2009 | Shahriari | |
| 2009/0062766 A1 | 3/2009 | Howlett et al. | |
| 2009/0149818 A1 | 6/2009 | Timm | |
| 2009/0149819 A1 | 6/2009 | Chelak | |
| 2009/0281556 A1 | 11/2009 | Newell et al. | |
| 2010/0000040 A1 | 1/2010 | Shaw et al. | |
| 2010/0047123 A1 | 2/2010 | Solomon et al. | |
| 2010/0049170 A1 | 2/2010 | Solomon et al. | |
| 2010/0050351 A1 | 3/2010 | Colantonio et al. | |
| 2010/0172794 A1 | 7/2010 | Ferlic et al. | |
| 2010/0204648 A1 | 8/2010 | Stout et al. | |
| 2010/0204652 A1 | 8/2010 | Morrissey et al. | |
| 2010/0292656 A1 | 11/2010 | Roger et al. | |
| 2010/0292673 A1 | 11/2010 | Korogi et al. | |
| 2011/0150958 A1 | 6/2011 | Davis et al. | |
| 2011/0160662 A1 | 6/2011 | Stout et al. | |
| 2011/0213341 A1 * | 9/2011 | Solomon | A61M 39/165 604/533 |
| 2011/0265825 A1 | 11/2011 | Rogers et al. | |

(56) References Cited

U.S. PATENT DOCUMENTS

| | | |
|---|---|---|
| 2012/0039765 A1 | 2/2012 | Solomon et al. |
| 2012/0197200 A1 | 8/2012 | Belson |
| 2012/0302997 A1* | 11/2012 | Gardner ............... A61M 39/20 604/533 |
| 2013/0090607 A1 | 4/2013 | McKinnon et al. |
| 2013/0165867 A1 | 6/2013 | Isaacson et al. |
| 2013/0310751 A1 | 11/2013 | Davis et al. |
| 2013/0331799 A1 | 12/2013 | Dasbach et al. |
| 2014/0135703 A1 | 5/2014 | Yeh et al. |
| 2014/0163516 A1 | 6/2014 | Lareau |
| 2014/0350485 A1 | 11/2014 | Sonderegger et al. |
| 2014/0364809 A1 | 12/2014 | Isaacson et al. |
| 2015/0343179 A1 | 12/2015 | Schumacher |
| 2015/0360005 A1 | 12/2015 | Arellano et al. |
| 2015/0374931 A1 | 12/2015 | Sugiki et al. |
| 2016/0106970 A1 | 4/2016 | Fangrow |
| 2016/0184558 A1 | 6/2016 | Raulerson et al. |
| 2016/0331937 A1 | 11/2016 | Teoh |

FOREIGN PATENT DOCUMENTS

| | | |
|---|---|---|
| CN | 103285450 A | 9/2013 |
| CN | 203525076 U | 4/2014 |
| EP | 1649890 A1 | 4/2006 |
| EP | 2606930 A1 | 6/2013 |
| EP | 2952220 A1 | 12/2015 |
| JP | H09103492 A | 4/1997 |
| JP | H10507946 A | 8/1998 |
| JP | 2001258713 A | 9/2001 |
| JP | 2002503968 A | 2/2002 |
| JP | 5867703 B2 | 2/2016 |
| JP | 2017503598 A | 2/2017 |
| WO | 8700441 A1 | 1/1987 |
| WO | 9929173 A1 | 6/1999 |
| WO | 2007044760 A2 | 4/2007 |
| WO | 2008157092 A1 | 12/2008 |
| WO | 2010039171 A1 | 4/2010 |
| WO | 2010143693 A1 | 12/2010 |
| WO | 2011053924 A1 | 5/2011 |
| WO | 2011066586 A1 | 6/2011 |
| WO | 2011115048 A1 | 9/2011 |
| WO | 2017074675 A1 | 5/2017 |
| WO | 2017074677 A1 | 5/2017 |
| WO | 2018067161 A1 | 4/2018 |
| WO | 2019018479 A1 | 1/2019 |

OTHER PUBLICATIONS

Decision, Institution of Inter Partes Review, 37 C.F.R. .sctn. 42,108, USPTO, Patent Trial and Appeal Board, *Excelsior Medical Corporation v. Becton, Dickinson and Company*, Case IPR2014-00880, U.S. Pat. No. 8,740,864, pp. 1-21, Nov. 25, 2014.

Patent Owner's Preliminary Response Under 37 C.F.R. .sctn. 42,10, USPTO, Patent Trial and Appeal Board, *Excelsior Medical Corporation v. Becton, Dickinson and Company*, Case IPR2014-00880, U.S. Pat. No. 8,740,864, pp. 1-30, Sep. 16, 2014.

\* cited by examiner

IV ACCESS PORT CAP FOR PROVIDING ANTIMICROBIAL PROTECTION

RELATED APPLICATIONS

This application is a continuation of U.S. application Ser. No. 17/374,729, filed Jul. 13, 2021, entitled IV ACCESS PORT CAP FOR PROVIDING ANTIMICROBIAL PROTECTION, which is a continuation of U.S. application Ser. No. 16/109,376, filed Aug. 22, 2018, entitled IV ACCESS PORT CAP FOR PROVIDING ANTIMICROBIAL PROTECTION, which is a continuation of U.S. application Ser. No. 15/674,389, filed Aug. 10, 2017, entitled IV ACCESS PORT CAP FOR PROVIDING ANTIMICROBIAL PROTECTION, which is a continuation of U.S. application Ser. No. 15/041,931, filed Feb. 11, 2016, entitled IV ACCESS PORT CAP FOR PROVIDING ANTIMICROBIAL PROTECTION, which is a continuation of U.S. application Ser. No. 14/185,827, filed Feb. 20, 2014, entitled IV ACCESS PORT CAP FOR PROVIDING ANTIMICROBIAL PROTECTION, which are incorporated herein in their entirety.

BACKGROUND OF THE INVENTION

The present invention relates generally to caps for providing antimicrobial protection to an IV access port or other type of device having a female luer connection. In particular, the caps of the present invention can be used to distribute an antimicrobial solution within the intraluminal space of a female luer device.

Currently, there are various products available for capping a port of an intravenous device (e.g. a catheter or other infusion device). In this specification, port will be used generally to describe any type of connector for interconnecting two devices. For example, FIG. 1 generally illustrates a port 100 that is configured as a female luer lock connector, while FIG. 2 generally illustrates a port 200 that is configured as a needleless female luer connector. Typically, a needleless connector employs a valve that seals the lumen of the device from the exterior environment and which is pierced or otherwise separated by a male connector to obtain access to the lumen.

In this specification, a female luer connector should be interpreted as any connector having an internal lumen that is tapered to conform to a corresponding male connector having the same or similar degree of tapering. These female luer connectors can include luer lock and luer slip (or non-lock luer) connectors.

Intravenous devices can employ ports to provide quick access to a patient's vasculature. These ports also enable the device to remain within the patient's vasculature even when no access to the vasculature is needed. When a port of an intravenous device is not in use, it is desirable to maintain the port clean and free from bacteria and other microbes. If the port becomes contaminated with microbes while not in use, it is possible that the microbes will be flushed into the patient's vasculature once the port is again used for accessing the patient's vasculature. Accordingly, maintaining a sterile port is essential to minimize the risk of infection.

To maintain the sterility of a port, various types of caps have been designed. These caps typically contain an antimicrobial solution that is applied to the exterior surfaces of the port when a cap is attached to the port. For example, some caps employ an alcohol-soaked material that is disposed within the cavity of the cap so that the material scrubs the exterior surfaces of the port when the cap is screwed on. Once screwed on, these caps can retain an amount of the antimicrobial solution around the exterior surface of the port to ensure that the exterior surface remains sterile until the cap is removed.

These caps have proven to be effective for disinfecting the exterior surfaces of the port. However, current designs only disinfect the exterior surfaces. Any microbes that may exist within the intraluminal space will likely remain even after these current caps are used.

Alternatively, to address this risk of infection, some ports are configured to have antimicrobial coatings on the intraluminal surfaces. With such coatings, the intraluminal surfaces can remain sterile even if microbes come in contact with the surfaces. These coatings can also dissolve into the fluid within the lumen to effectively spread antimicrobial agents throughout the lumen. However, there are various drawbacks to using antimicrobial coatings on the intraluminal surfaces of ports. For example, ports that employ antimicrobial coatings are significantly more expensive to produce. As a result many facilities choose not to use them. Also, for a coating to be effective, it must retain its antimicrobial properties for at least the amount of time that the port could possibly be used (e.g. up to 7 days). To accomplish this, relatively thick coatings or highly concentrated coatings are used. This causes the concentration of antimicrobial agents to be very high during the initial usage time which poses a toxicity risk.

BRIEF SUMMARY OF THE INVENTION

The present invention extends to caps for providing antimicrobial protection to a female luer port of an intravenous device. The caps of the present invention are designed to distribute an antimicrobial solution within the intraluminal surfaces of the port. Additionally, in some embodiments, the caps are designed to also distribute an antimicrobial solution around the exterior surfaces of the port. Accordingly, the caps of the present invention provide a complete solution for disinfecting a port of an intravenous device.

In one embodiment, the present invention is implemented as a cap for a port of an intravenous device. The cap can comprise a body having a cavity; an actuator positioned within the cavity; and an absorbent material containing an antimicrobial solution. The absorbent material is contained within the cavity between the actuator and an inner surface of the body. When the cap is connected to a port of an intravenous device, the actuator is forced into the cavity and compresses the absorbent material causing the antimicrobial solution to flow onto an intraluminal surface of the port.

In some embodiments, the actuator comprises a lumen through which the antimicrobial solution flows to reach a lumen of the port.

In some embodiments, the actuator comprises a male luer in which the lumen is formed.

In some embodiments, the antimicrobial solution flows through a gap between the body and an exterior surface of the actuator and onto an exterior surface of the port.

In some embodiments, the body includes a seal that the actuator contacts when the cap is connected to the port thereby forming a seal between the actuator and the body.

In some embodiments, the concentration of an antimicrobial agent within the antimicrobial solution is selected such that when the antimicrobial solution mixes with fluid contained within the lumen of the port, the concentration of the antimicrobial agent remains higher than the minimum inhibitory concentration of the antimicrobial agent.

In some embodiments, the port is a female luer into which the actuator inserts.

In some embodiments, the port is a needleless connector into which the actuator inserts.

In some embodiments, the actuator includes a protrusion that is positioned within a lumen in the body, the protrusion having a lumen through which the antimicrobial solution flows.

In some embodiments, the actuator includes a plurality of prongs that extend through corresponding openings in the body.

In some embodiments, the antimicrobial solution flows through the openings when the actuator is forced into the cavity.

In some embodiments, the actuator includes a lumen that has an antimicrobial coating.

In another embodiment, the present invention is implemented as a cap for a port of an intravenous device. The cap can comprise a body having a cavity; an actuator positioned within the cavity, the actuator having a lumen; and an absorbent material containing an antimicrobial solution, the absorbent material being contained within the cavity between the actuator and an inner surface of the body. Prior to the cap being connected to a port of an intravenous device, the absorbent material remains uncompressed. Then, when the cap is connected to a port of an intravenous device, the actuator compresses the absorbent material causing the antimicrobial solution to flow through the lumen of the actuator and into a lumen of the port.

In some embodiments, the actuator is sized such that a gap exists between an outer edge of the actuator and a wall of the cavity, the antimicrobial solution also flowing through the gap onto an exterior surface of the port.

In some embodiments, the actuator includes a plurality of prongs which extend through corresponding openings in the body. The antimicrobial solution flows through the openings onto the exterior surface of the port In some embodiments, the body includes a seal for sealing the lumen of the actuator.

In some embodiments, the actuator comprises a male luer.

In another embodiment, the present invention is implemented as a cap for a needleless connector of an intravenous device. The cap can comprise a body having a cavity; an absorbent material positioned within the cavity, the absorbent material containing an antimicrobial solution; and an actuator positioned within the cavity against the absorbent material. The actuator is moveable within the cavity to compress the absorbent material such that upon the cap being connected to a needleless connector, the needleless connector causes the actuator to compress the absorbent material releasing the antimicrobial solution onto an intraluminal surface of the needleless connector.

In some embodiments, the actuator comprises a lumen. The antimicrobial solution flows through the lumen of the actuator onto the intraluminal surface of the needleless connector.

In some embodiments, the antimicrobial solution also flows around an exterior surface of the actuator onto an exterior surface of the needleless connector.

This summary is provided to introduce a selection of concepts in a simplified form that are further described below in the Detailed Description. This Summary is not intended to identify key features or essential features of the claimed subject matter.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 7A illustrates the cap prior to contacting the port. FIG. 7B illustrates that, as the cap is being forced onto the port, the actuator is forced into the absorbent material causing antimicrobial solution to flow towards the port through the gaps formed by the movement of the actuator and through the lumen of the actuator. FIG. 7C illustrates that, once the cap is fully connected to the port, the actuator is forced against a seal to seal the lumen of the port.

FIG. 11A illustrates the cap upon contacting the port.

FIG. 11B illustrates that, as the cap is being forced onto the port, the actuator is forced into the absorbent material causing antimicrobial solution to flow towards the port through the gaps formed by the movement of the actuator and through the lumen of the actuator. FIG. 11C illustrates that, once the cap is fully connected to the port, the actuator is forced against a seal to cause further flow of the antimicrobial solution to be only through the lumen of the actuator.

DETAILED DESCRIPTION OF THE INVENTION

Figure 1:
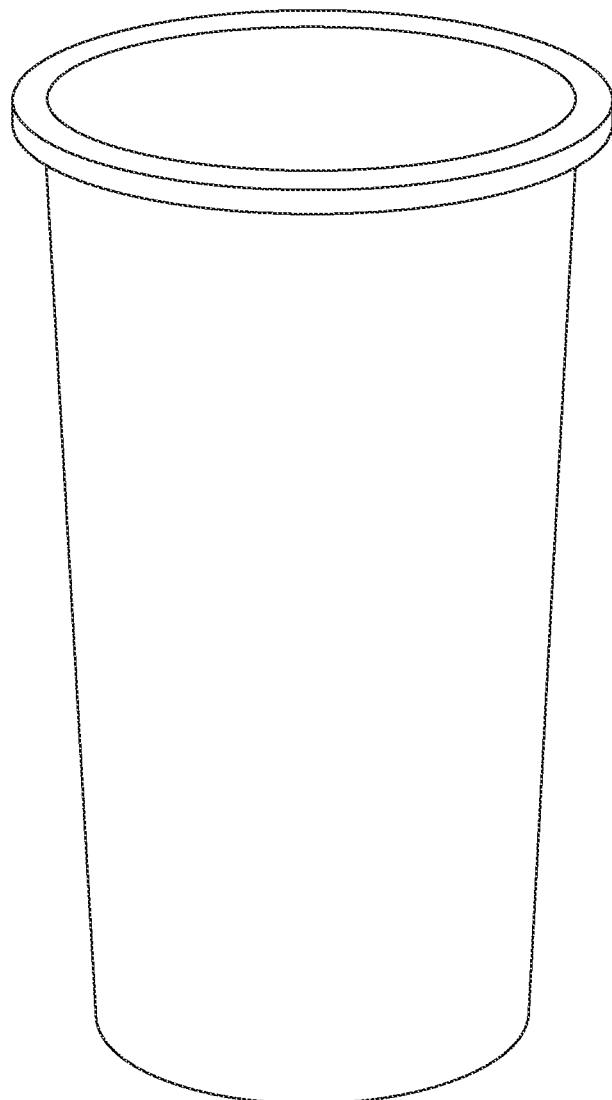
FIG. 1 illustrates a perspective view of an example of a prior art port that is configured as a female luer lock connector.
Figure 2:
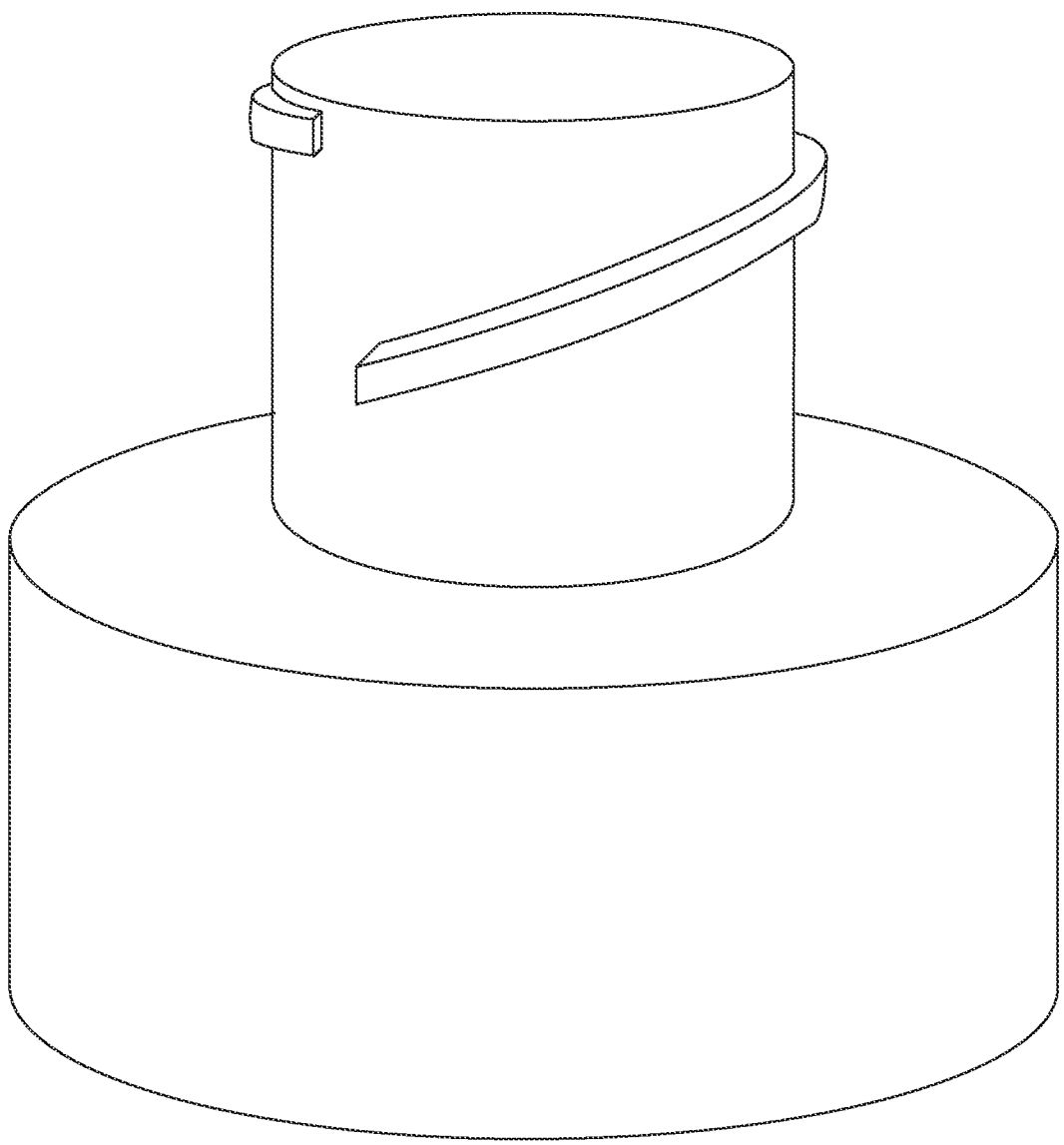
FIG. 2 illustrates a perspective view of an example of a prior art port that is configured as a needleless female luer connector.

The present invention extends to caps for providing antimicrobial protection to a female luer port of an intravenous device. The caps of the present invention are designed to distribute an antimicrobial solution within the intraluminal surfaces of the port. Additionally, in some embodiments, the caps are designed to also distribute an antimicrobial solution around the exterior surfaces of the port. Accordingly, the caps of the present invention provide a complete solution for disinfecting a port of an intravenous device.

In one embodiment, the present invention is implemented as a cap for a port of an intravenous device. The cap can comprise a body having a cavity; an actuator positioned within the cavity; and an absorbent material containing an antimicrobial solution. The absorbent material is contained within the cavity between the actuator and an inner surface of the body. When the cap is connected to a port of an intravenous device, the actuator is forced into the cavity and compresses the absorbent material causing the antimicrobial solution to flow onto an intraluminal surface of the port.

In some embodiments, the actuator comprises a lumen through which the antimicrobial solution flows to reach a lumen of the port.

In some embodiments, the actuator comprises a male luer in which the lumen is formed.

In some embodiments, the antimicrobial solution flows through a gap between the body and an exterior surface of the actuator and onto an exterior surface of the port.

In some embodiments, the body includes a seal that the actuator contacts when the cap is connected to the port thereby forming a seal between the actuator and the body.

In some embodiments, the concentration of an antimicrobial agent within the antimicrobial solution is selected such that when the antimicrobial solution mixes with fluid contained within the lumen of the port, the concentration of the antimicrobial agent remains higher than the minimum inhibitory concentration of the antimicrobial agent.

In some embodiments, the port is a female luer into which the actuator inserts.

In some embodiments, the port is a needleless connector into which the actuator inserts.

In some embodiments, the actuator includes a protrusion that is positioned within a lumen in the body, the protrusion having a lumen through which the antimicrobial solution flows.

In some embodiments, the actuator includes a plurality of prongs that extend through corresponding openings in the body.

In some embodiments, the antimicrobial solution flows through the openings when the actuator is forced into the cavity.

In some embodiments, the actuator includes a lumen that has an antimicrobial coating.

In another embodiment, the present invention is implemented as a cap for a port of an intravenous device. The cap can comprise a body having a cavity; an actuator positioned within the cavity, the actuator having a lumen; and an absorbent material containing an antimicrobial solution, the absorbent material being contained within the cavity between the actuator and an inner surface of the body. Prior to the cap being connected to a port of an intravenous device, the absorbent material remains uncompressed. Then, when the cap is connected to a port of an intravenous device, the actuator compresses the absorbent material causing the antimicrobial solution to flow through the lumen of the actuator and into a lumen of the port.

In some embodiments, the actuator is sized such that a gap exists between an outer edge of the actuator and a wall of the cavity, the antimicrobial solution also flowing through the gap onto an exterior surface of the port.

In some embodiments, the actuator includes a plurality of prongs which extend through corresponding openings in the body. The antimicrobial solution flows through the openings onto the exterior surface of the port In some embodiments, the body includes a seal for sealing the lumen of the actuator.

In some embodiments, the actuator comprises a male luer.

In another embodiment, the present invention is implemented as a cap for a needleless connector of an intravenous device. The cap can comprise a body having a cavity; an absorbent material positioned within the cavity, the absorbent material containing an antimicrobial solution; and an actuator positioned within the cavity against the absorbent material. The actuator is moveable within the cavity to compress the absorbent material such that upon the cap being connected to a needleless connector, the needleless connector causes the actuator to compress the absorbent material releasing the antimicrobial solution onto an intraluminal surface of the needleless connector.

In some embodiments, the actuator comprises a lumen. The antimicrobial solution flows through the lumen of the actuator onto the intraluminal surface of the needleless connector.

In some embodiments, the antimicrobial solution also flows around an exterior surface of the actuator onto an exterior surface of the needleless connector.

Figure 3:
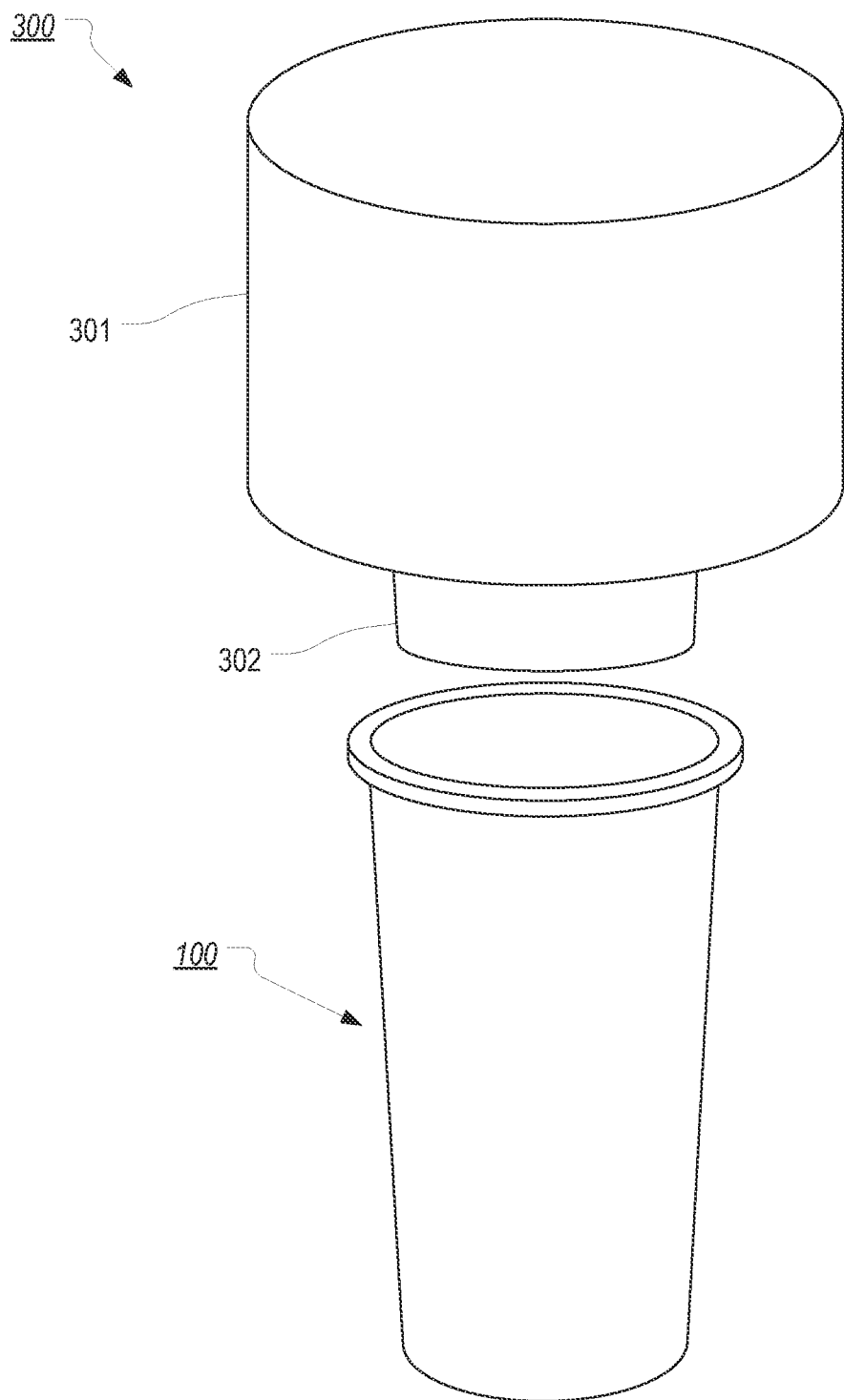
FIG. 3 illustrates a perspective view of a cap in accordance with one or more embodiments of the invention that may be used to apply an antimicrobial solution to the intraluminal surfaces of a port.
Figure 4:
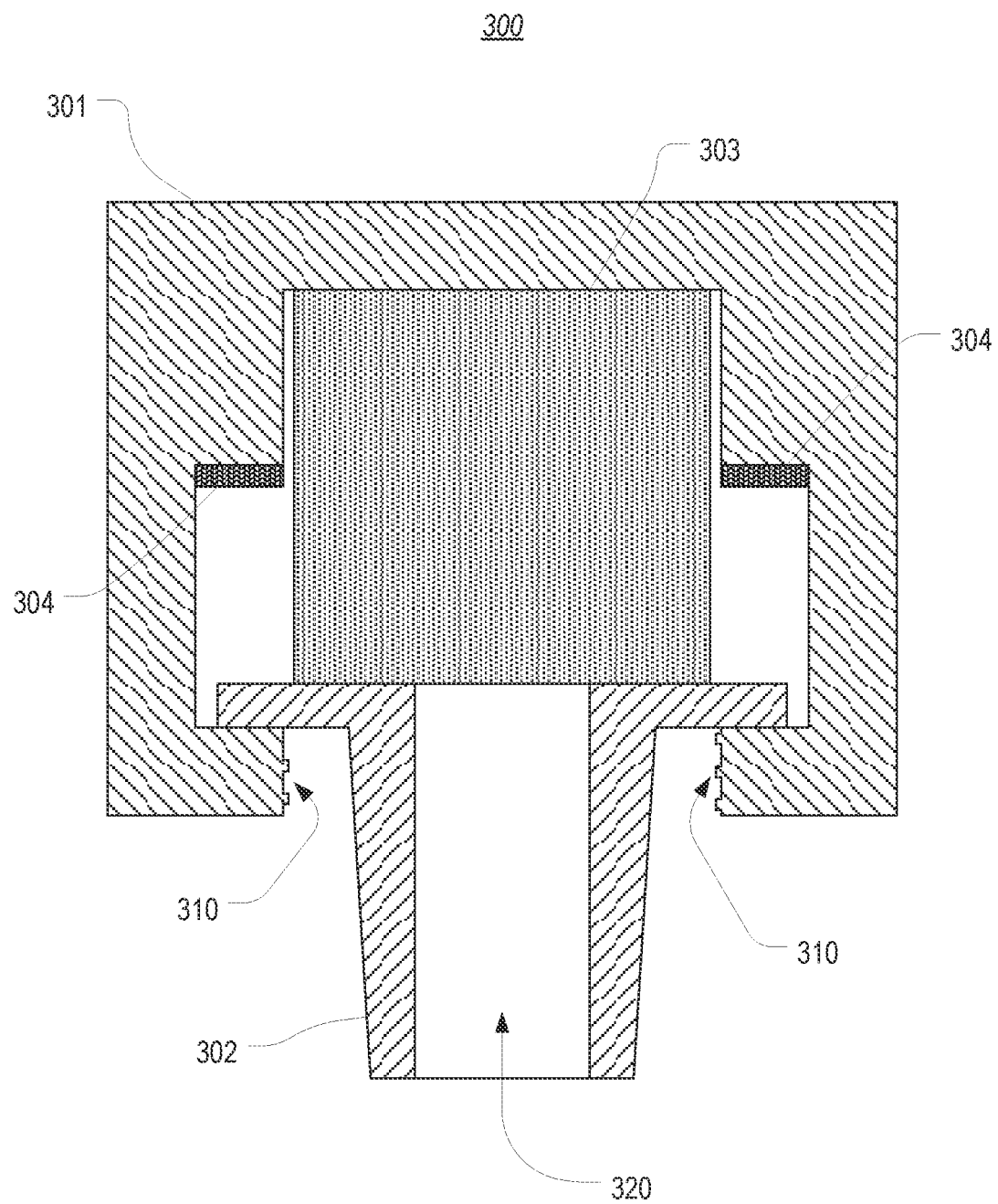
FIG. 4 illustrates a cross-sectional view of a cap in accordance with one or more embodiments of the invention in which an actuator is movable within the body of the cap to cause an antimicrobial solution to be squeezed from an absorbent material contained within the body and distributed through the actuator into the intraluminal space of a port.

FIG. 3 illustrates a perspective view of a cap 300 in accordance with one or more embodiments of the invention. As shown, cap 300 comprises a body 301 and an actuator 302. Body 301 is generally shaped to allow cap 300 to be connected to a female luer connector such as port 100. If the cap is designed to connect to a female luer lock connector, the inside surface of the body can include threads (e.g. as shown in FIG. 4). In contrast, if the cap is designed to connect to a female luer slip connector, the inside surface of the body may or may not include threads. In either case, actuator 302 can be configured as a male luer connector to allow actuator 302 to be inserted into the female luer port 100.

FIG. 4 illustrates a cross-section view of cap 300. As shown, cap 300 includes body 301, actuator 302, and absorbent material 303 positioned between body 301 and actuator 302. Cap 300 includes threads 310 and is therefore an example of a cap designed for a female luer lock connector. Actuator 302 has a tip that is designed as a male luer connector to allow the tip to be inserted into the lumen of a female luer connector.

FIG. 4 depicts cap 300 prior to being connected to a port. Before connection, actuator 302 is positioned against the interior surface of body 301 and does not compress absorbent material 303. In some embodiments, actuator 302 can be held in this position by an adhesive, welding, or other physical force between body 301 and actuator 302. In other embodiments, actuator 302 can be held in this position by absorbent material 303. In other words, absorbent material 303 may be sufficiently rigid to retain the position of actuator 302 until a substantial force is applied against actuator 302. In any case, actuator 302 is designed to not compress absorbent material 303 until cap 300 is connected to a port. A seal (not shown) can be applied overtop of actuator 302 and possibly the opening of body 301 to seal absorbent material 303 from the exterior environment until cap 300 is to be used.

Figure 5:
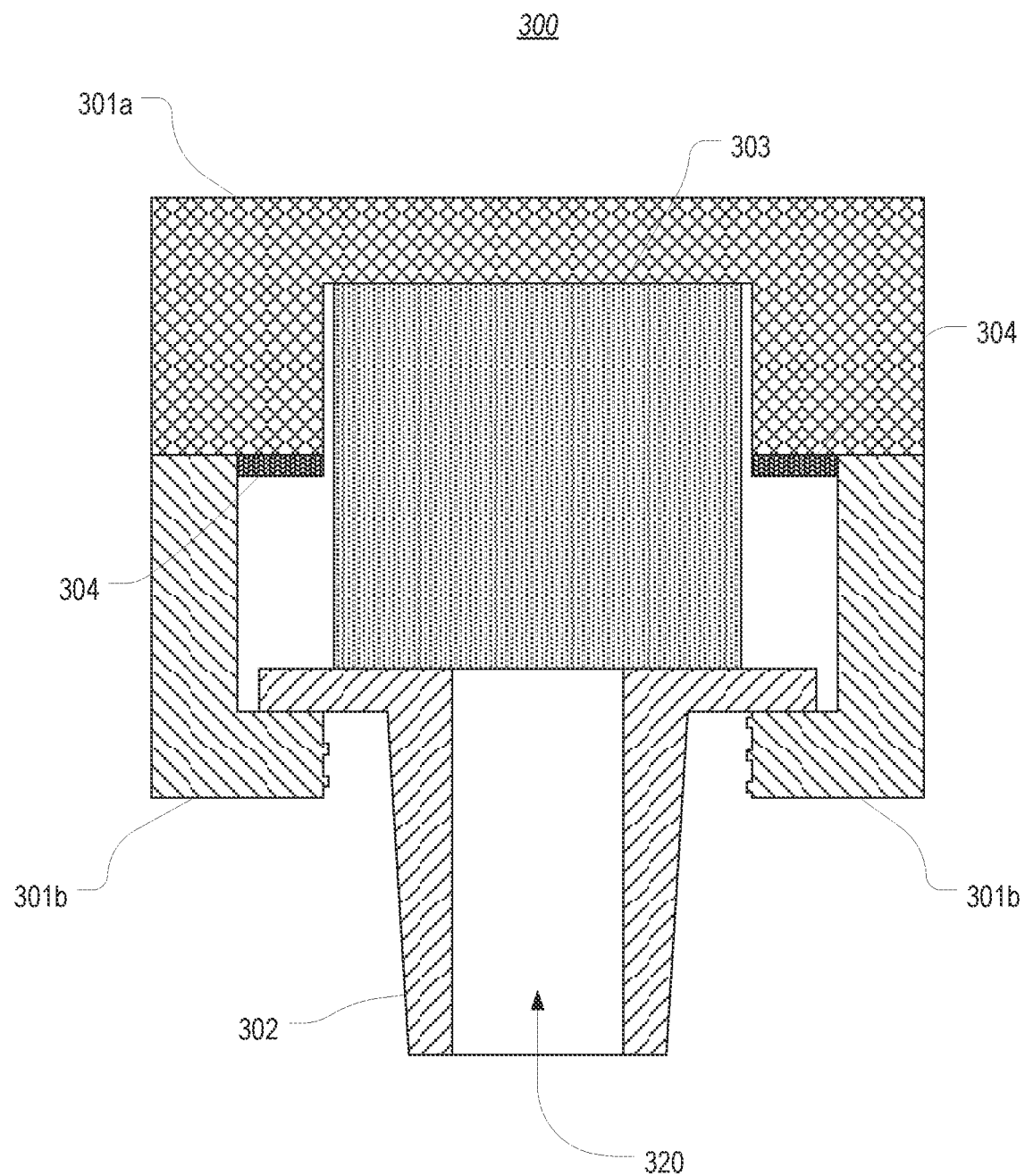
FIG. 5 illustrates a cross-sectional view of a cap having a body that is comprised of two pieces in accordance with one or more embodiments of the invention.

FIG. 5 illustrates a cross-sectional view of an alternate embodiment of cap 300. In this alternate embodiment, body 301 comprises two pieces, a top piece 301a and a bottom piece 301b. This two piece design can be used to facilitate manufacturing (e.g. to facilitate positioning actuator 302 within body 301). Whether the design of FIG. 4 or of FIG. 5 is employed, cap 300 will function the same as will be described below.

Figure 6:
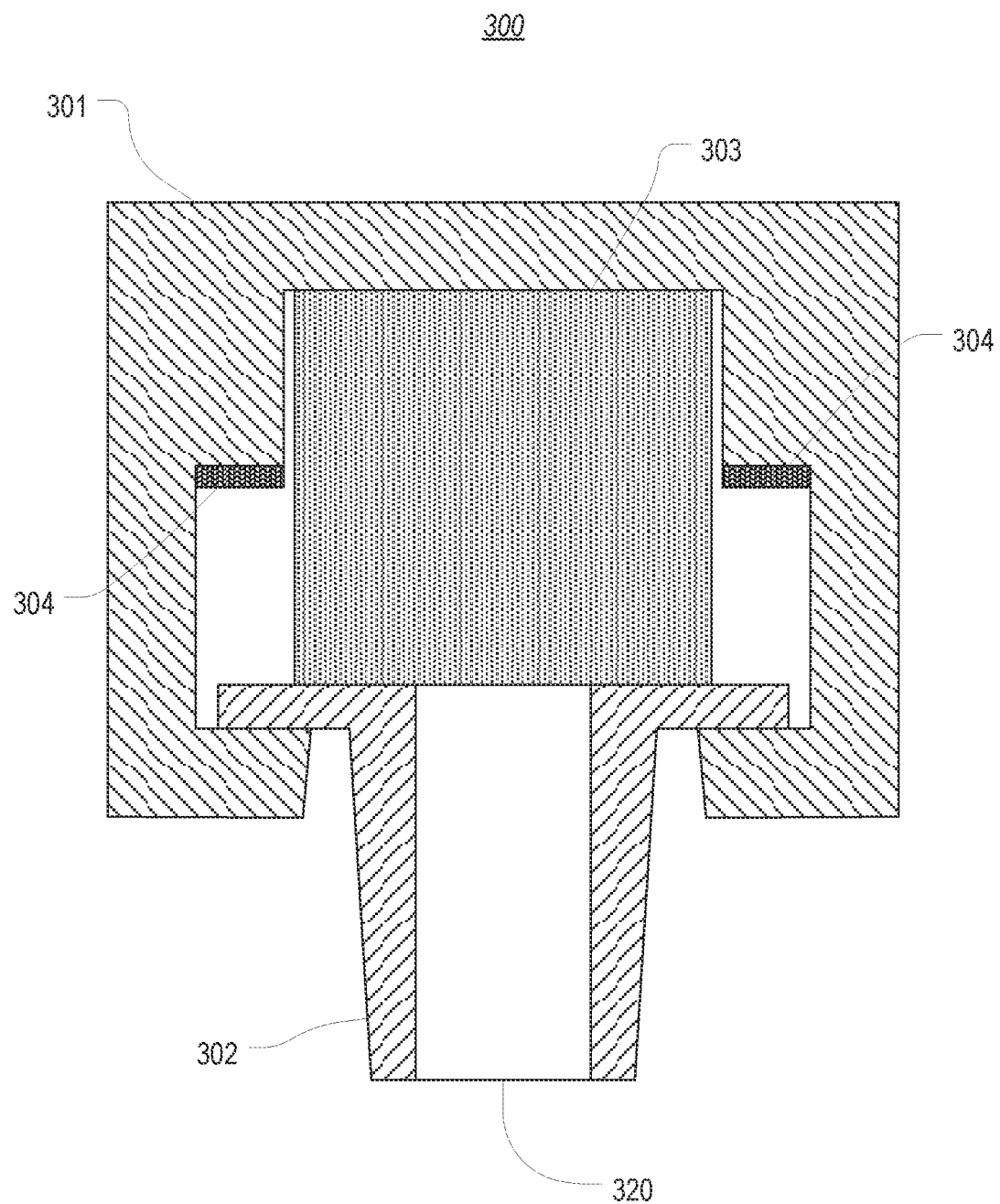
FIG. 6 illustrates a cross-sectional view of a cap that is configured to be connected to a port that is configured as a luer slip connector in accordance with one or more embodiments of the invention.

FIG. 6 illustrates a cross-sectional view of another alternate embodiment of cap 300. In this embodiment, body 301 does not include threads but is configured to form a friction fit with the exterior surface of a port. Accordingly, a cap in accordance with this alternate embodiment could be used on a non-lock female luer connector. Regardless of the type of port to which cap 300 will be connected, it is desirable to secure body 301 to the port (e.g. via threads or a friction fit) to allow a seal to be formed between actuator 302 and body 301 once the cap is connected. The role of this seal will be further described below with reference to FIG. 7C.

With continued reference to FIGS. 4-6, absorbent material 303 is saturated with an antimicrobial solution which remains within absorbent material 303 until absorbent material 303 is compressed. Actuator 302 is designed to provide a fluid pathway to distribute the antimicrobial solution to a port when cap 300 is connected to the port. The primary fluid pathway is through lumen 320. However, a secondary fluid pathway is also provided around the exterior of actuator 302. The distribution of the antimicrobial solution is illustrated in FIGS. 7A-7C.

Figure 7A:
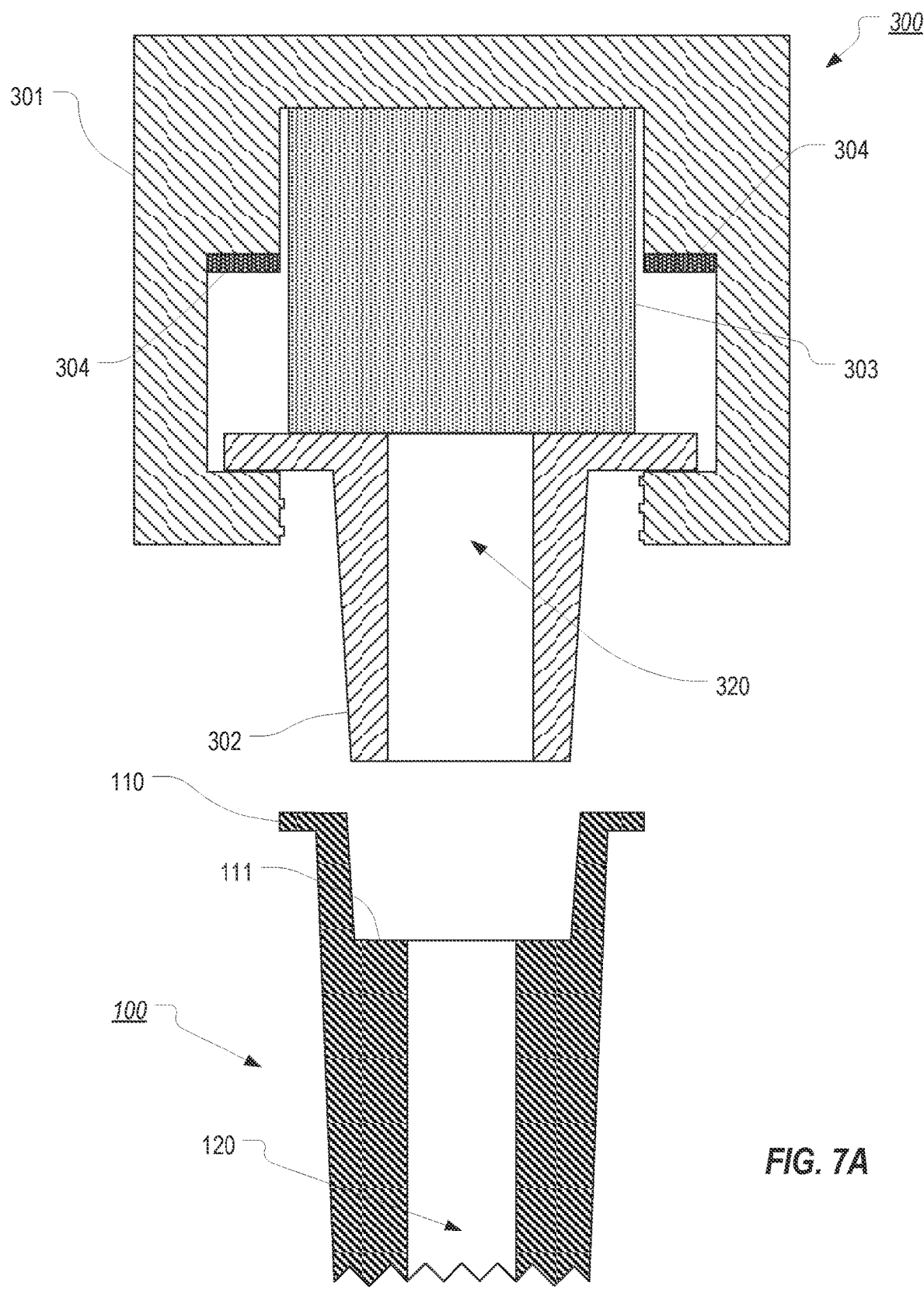
FIGS. 7A-7C illustrate a sequence of how the cap depicted in FIG. 4 is connected to a port of an intravenous device.
Figure 7B:
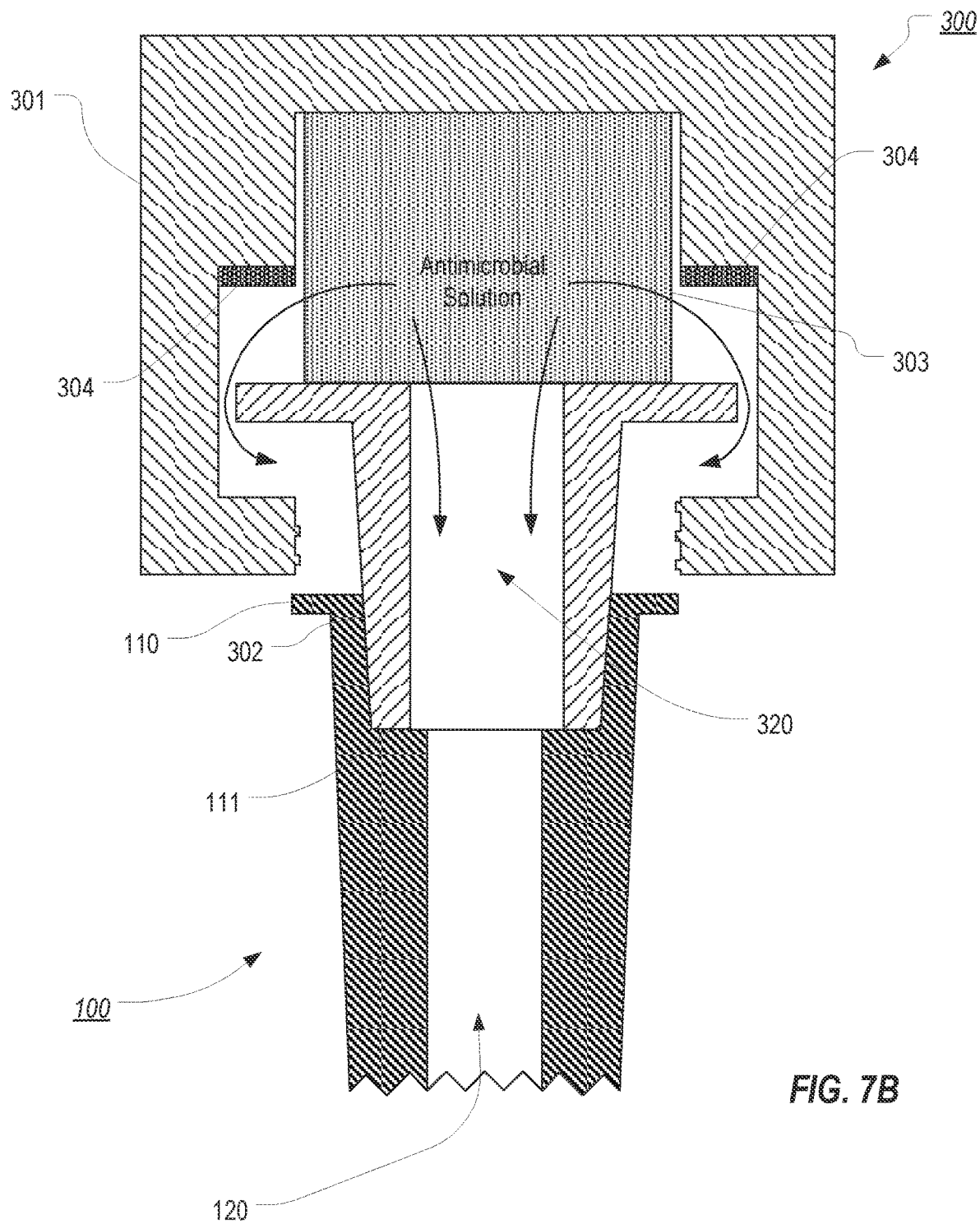
Figure 7C:
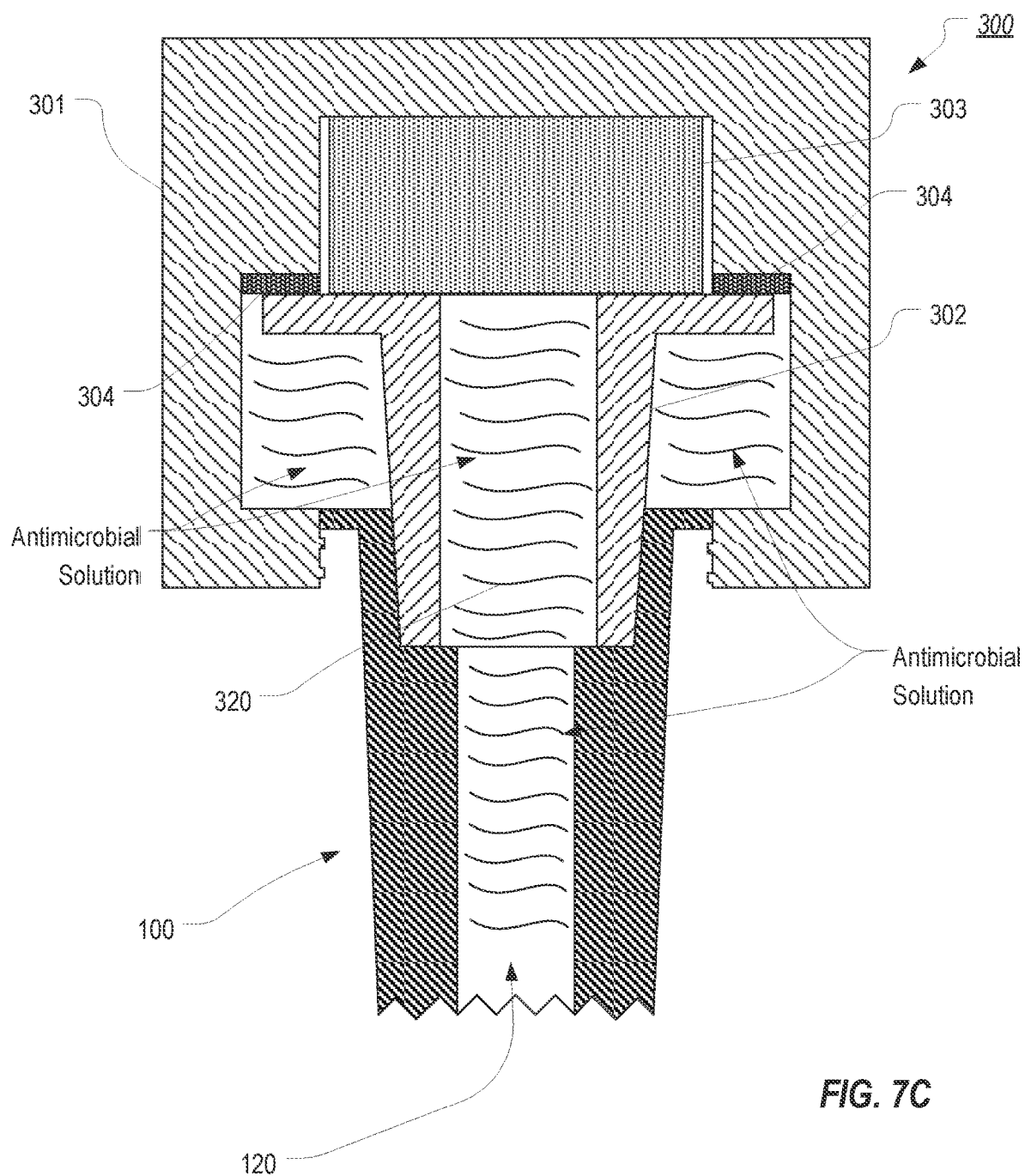

FIGS. 7A-7C illustrate a sequence that occurs when cap 300 is connected to a port. Although FIGS. 7A-7C illustrate the design of cap 300 as shown in FIG. 4, the same sequence would occur when a cap designed as shown in FIG. 5 or 6 is connected. Also, for simplicity of illustration, cap 300 is shown as being connected to port 100. However, the same sequence would occur when cap 300 is connected to any port that is configured as a female luer connector. Examples of ports on which cap 300 can be used include the BD Q-Syte® (manufactured by Becton, Dickinson and Company), the CareFusion MaxPlus® Clear (manufactured by CareFusion Corp), and the LifeShield MicroClave® (manufactured by Hospira, Inc.) among many others.

FIG. 7A shows the state of cap 300 prior to contacting port 100. In this state, cap 300 is as shown in FIG. 4. Port 100 is shown as including an internal ridge 111 against which the tip of actuator 302 presses when cap 300 is connected to the port. Port 100 is also shown as including threads 110 and is therefore an example of a luer lock connector. Accordingly, cap 300 is connected to port 100 by threading the cap onto the port.

As shown in FIG. 7B, as cap 300 is initially inserted into and advanced onto port 100, the tip of actuator 302 contacts ridge 111 of port 100. This contact forces actuator upward away from body 301 and into absorbent material 303. The compression of absorbent material 303 causes the antimicrobial solution to flow out of the absorbent material. The arrows in FIG. 7B indicate the pathways along which the absorbent material will flow.

The primary pathway along which the antimicrobial solution flows is through lumen 320 of actuator 302. Because lumen 320 aligns with lumen 120 of port 100, the antimicrobial solution flowing through lumen 320 will ultimately be distributed along the surfaces of lumen 120 and into any fluid contained within lumen 120. In this way, the intraluminal surfaces of port 100 can be disinfected.

The secondary pathway is around actuator 302 as depicted by the outer arrows in FIG. 7B. The antimicrobial solution will flow along the secondary pathway until the top surface of actuator 302 contacts seal 304 formed along the interior surface of body 301 as is shown in FIG. 7C. The contact between actuator 302 and seal 304 limits the antimicrobial solution from flowing around actuator 302 and therefore forces further flow through lumen 320. In this way, an adequate amount of antimicrobial solution will flow into the intraluminal space of port 100.

As shown in FIG. 7C, after cap 300 has been connected, antimicrobial solution will be contained within lumen 320 and lumen 120 as well as in the spaces between the outer surface of actuator 302, and the inner surface of body 301. This antimicrobial solution outside of actuator 302 can disinfect the top and outer surfaces of port 100. Because the connection between port 100 and cap 300 may not be fluid tight, the antimicrobial solution may be allowed to seep between threads 110 and 310 and onto the exterior surfaces of port 100. Also, in some embodiments where a tight seal is not form (or at least not formed initially when the antimicrobial solution flows around actuator 302) this antimicrobial solution can flow into the opening of port 100 between the exterior surface of actuator 302 and the interior surface of port 100. In this way, the intraluminal surfaces that may otherwise not be reached by antimicrobial solution that has flowed through lumen 320 may still be disinfected.

Accordingly, the design of cap 300 allows the intraluminal surfaces of a port to be disinfected. Because the lumen of port 100 may typically contain a fluid (e.g. a saline solution or other solution that was infused into the patient), the antimicrobial solution can mix with the fluid to enhance the distribution of the antimicrobial agents throughout lumen 120.

When cap 300 is fully connected to port 100, a seal can be formed between actuator 302 and seal 304 as shown in FIG. 7C. The tight fit between the male luer actuator 302 and the female luer port 100 can also form a seal between these two connectors. Accordingly, lumens 120 and 320 can be substantially sealed from the external environment thereby limiting the amount of antimicrobial solution within lumen 120 that evaporates after cap 300 has been connected. The antimicrobial solution can therefore remain active until the cap is removed for attachment of another device. In this way, when another device is connected to the port, the antimicrobial solution that remains within lumen 120 can disinfect the tip of the device. Accordingly, cap 300 not only disinfects port 100 when not in use, but can also disinfect other devices that are connected to the port after cap 300 has been removed.

Figure 8:
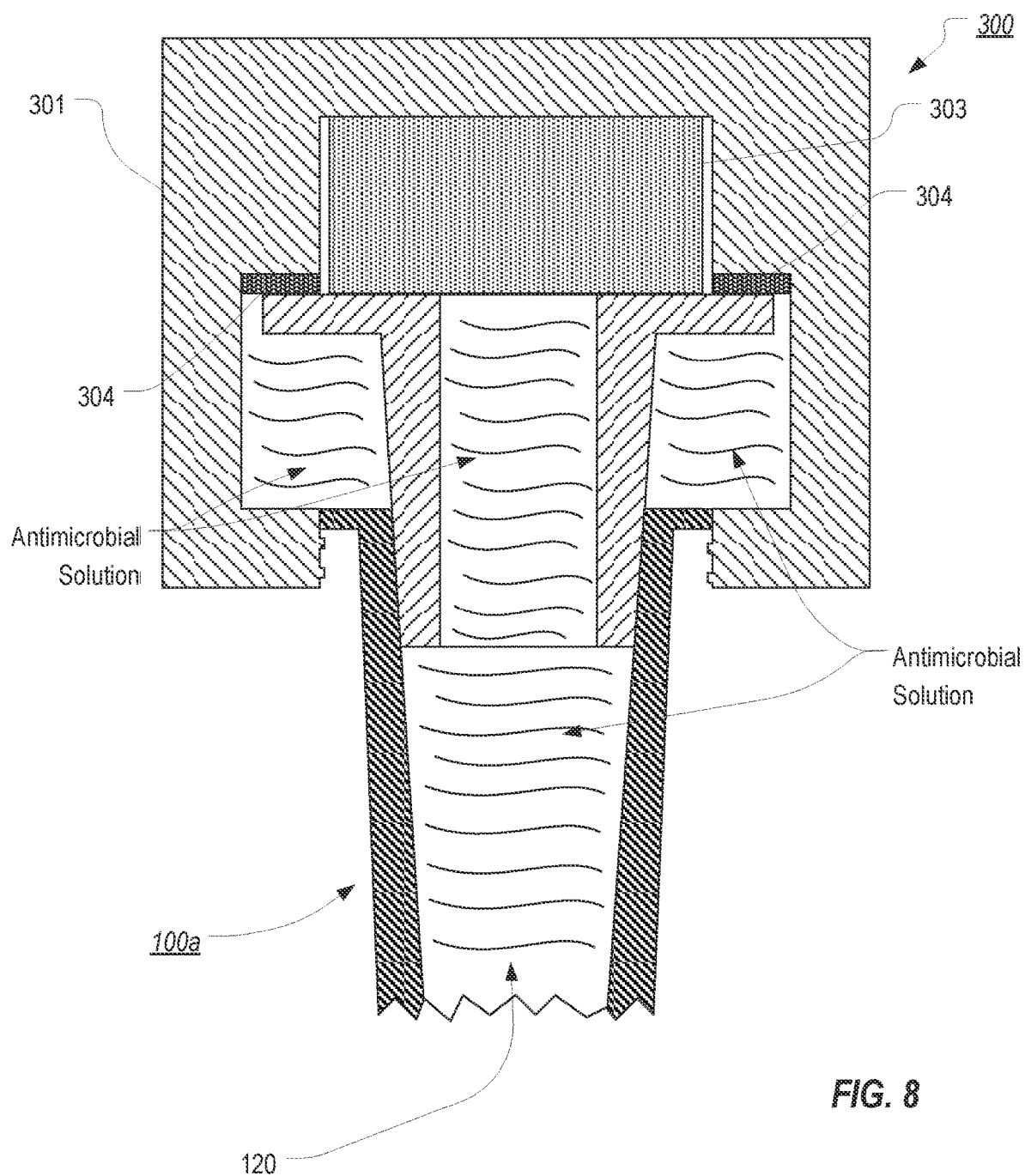
FIG. 8 illustrates a cross-sectional view of the cap depicted in FIG. 4 when connected to a port that does not include a ridge against which the actuator presses.

FIG. 8 illustrates a cross-sectional view of an alternate embodiment in which a port 100a does not include a ledge against which the tip of actuator 302 presses. In such cases, the frictional force created when actuator 302 has been inserted into lumen 120 can be sufficient to force actuator 302 upward into absorbent material 303. This frictional force can also be sufficient to form a seal between actuator 302 and port 100.

Figure 9A:
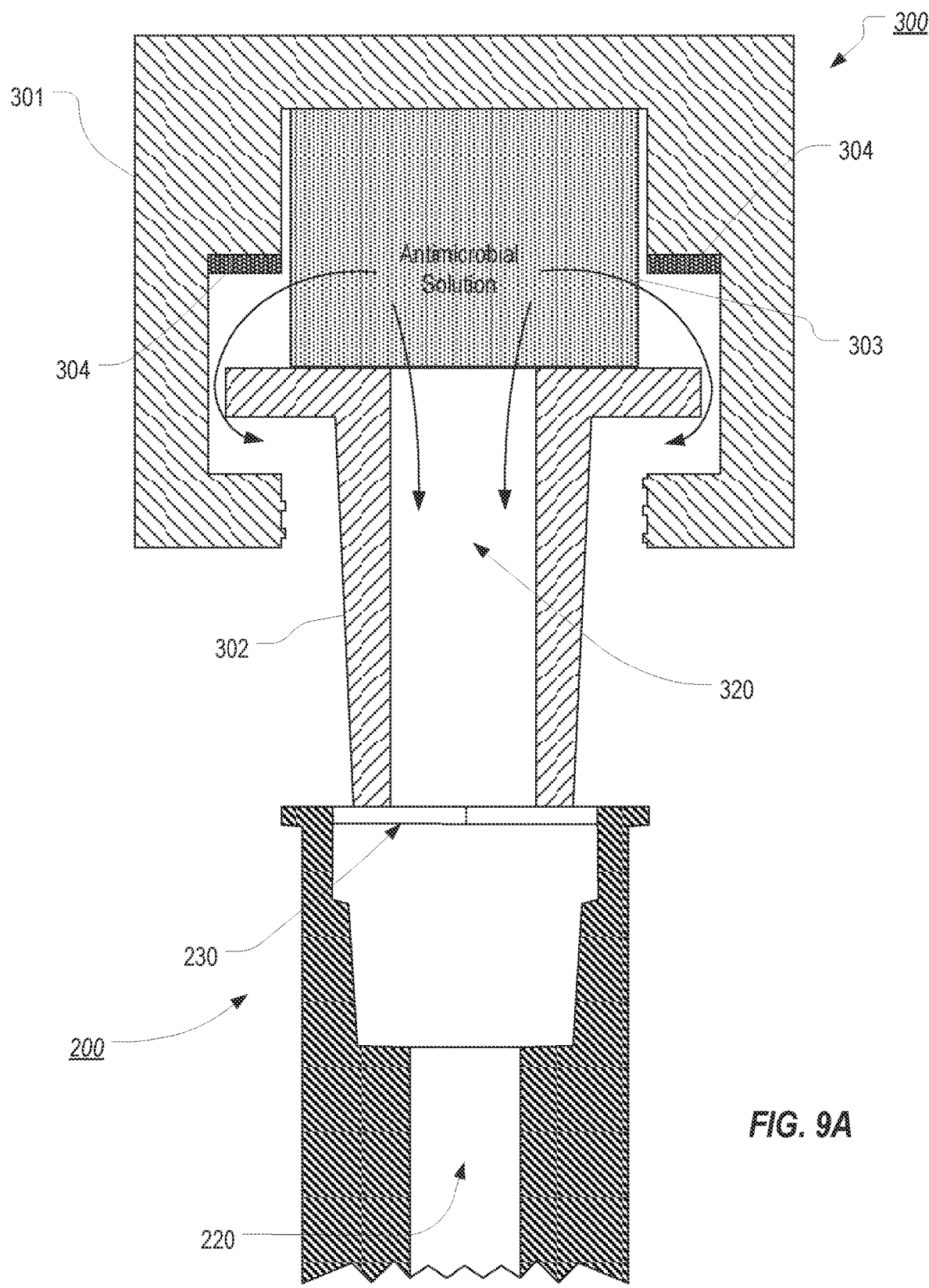
FIGS. 9A and 9B illustrate a sequence of how the cap depicted in FIG. 4 can be used on a port that employs a septum.
Figure 9B:
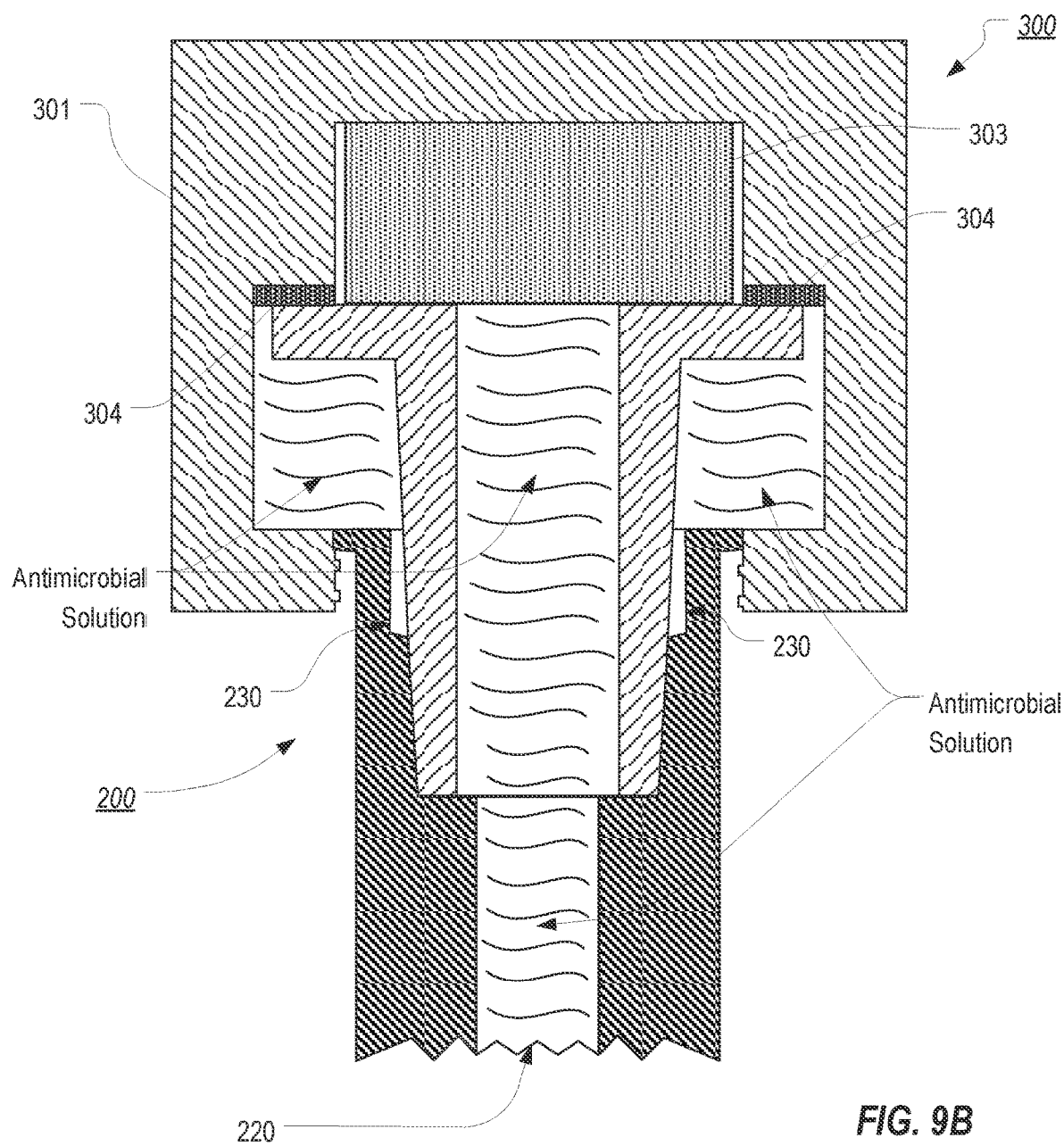

FIGS. 9A and 9B illustrate a cross-sectional view of another alternate embodiment in which cap 300 is connected to a port 200 that is configured as a needleless connector that includes a split septum 230. As shown in FIG. 9A, as the tip of actuator 302 initially contacts septum 230 and is forced through septum 230, actuator 302 is forced upwardly to initiate the flow of antimicrobial solution. Actuator 302 will pass through septum 230 and ultimately contact a ledge within lumen 220 of port 200 (or if port 200 does not contain a ledge, may contact the tapered sides of the port). As shown in FIG. 9B, when fully connected, cap 300 is positioned in a similar manner on port 200 as cap 300 is positioned on port 100. Accordingly, cap 300 can be used to disinfect the intraluminal surfaces of ports of various designs and configurations.

Figure 10A:
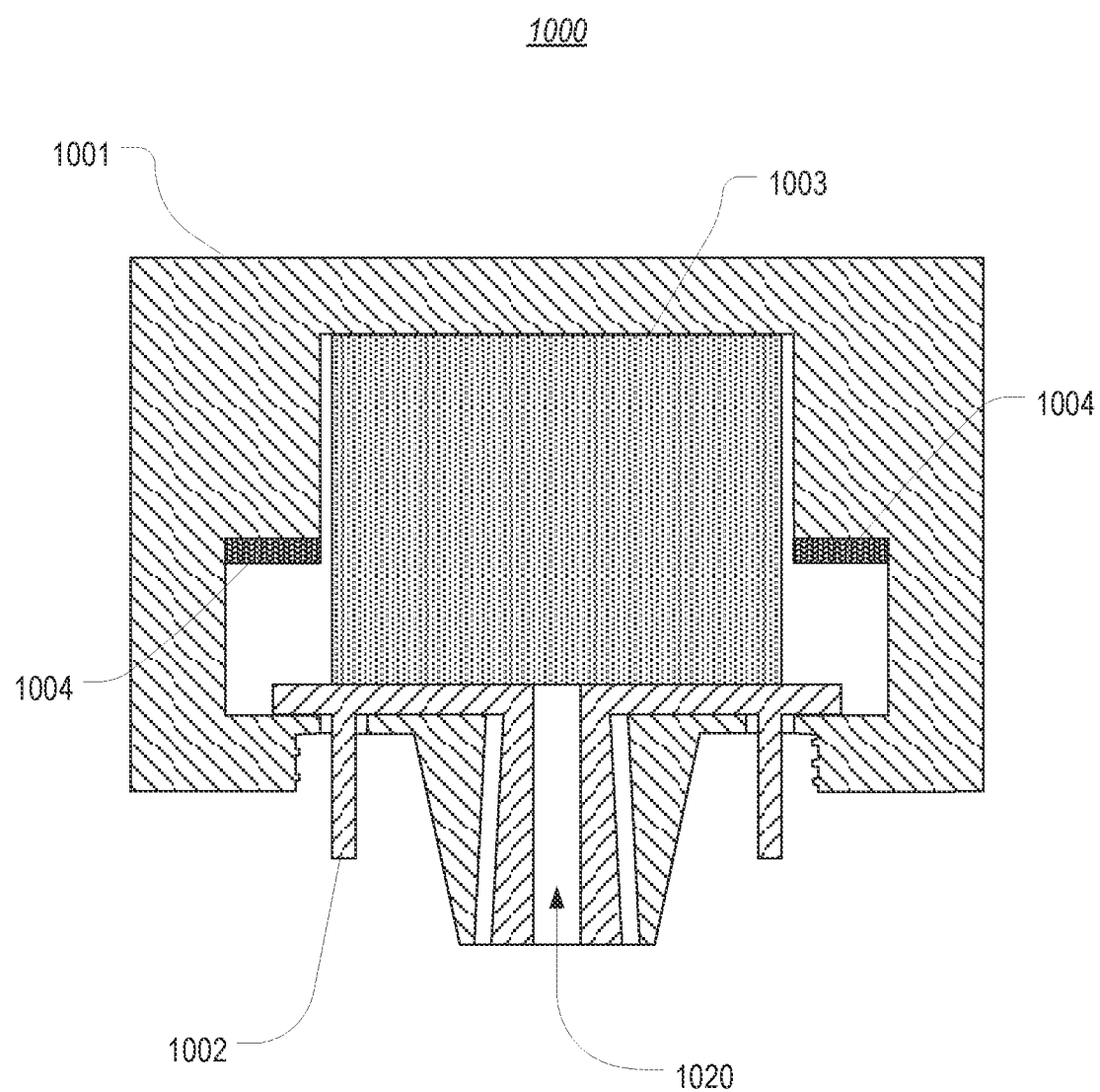
FIG. 10A illustrates a cross-sectional view of an alternate embodiment of a cap which employs prongs to facilitate the flow of antimicrobial solution to the exterior surfaces of the port.

FIG. 10A illustrates a cross-sectional view of another embodiment of a cap 1000. Cap 1000, like cap 300, includes a body 1001, an actuator 1002, and absorbent material 1003. However, actuator 1002 and the bottom surface of body 1001 have a different configuration to enhance the flow of absorbent material to the exterior surfaces of a port.

Figure 10B:
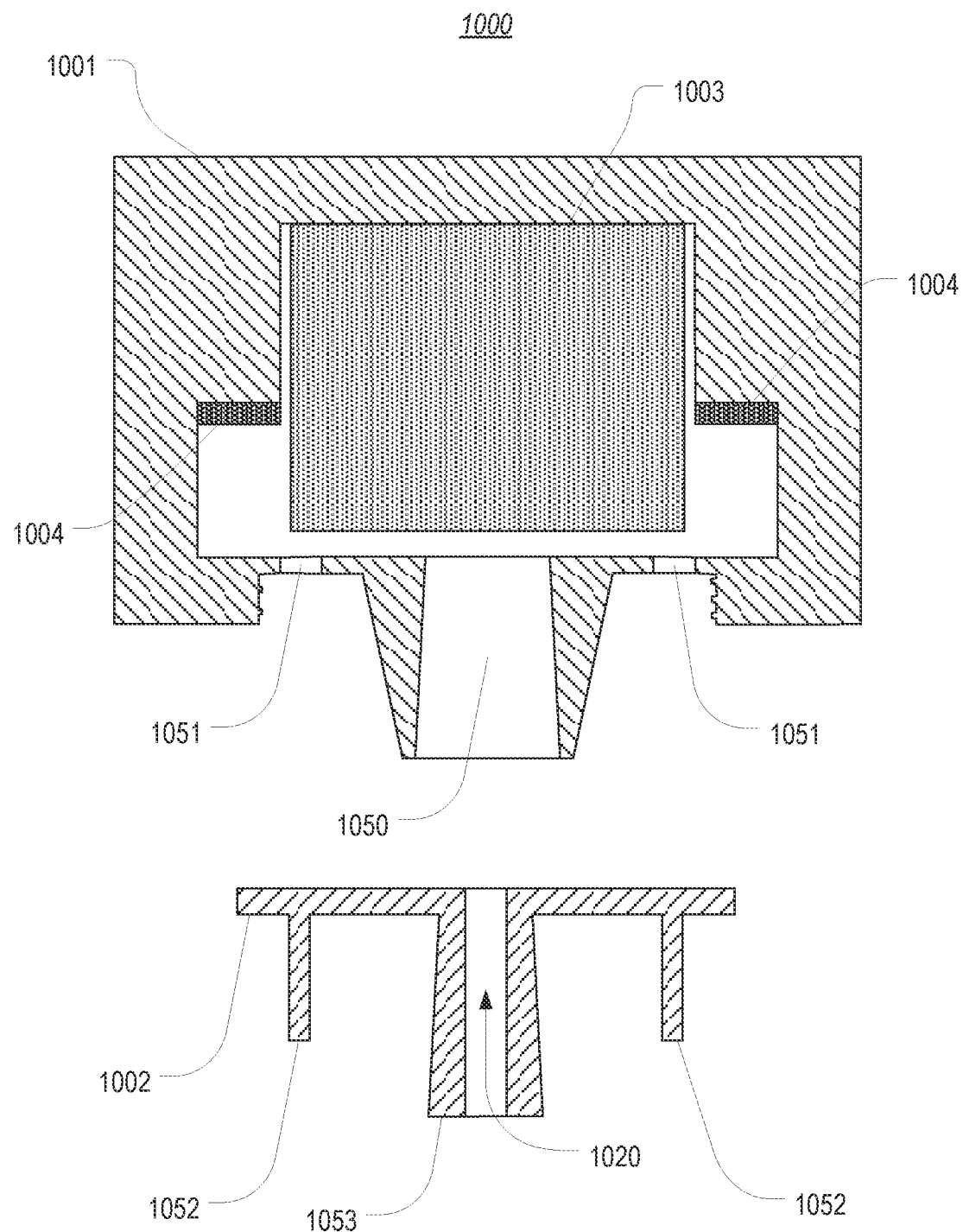
FIG. 10B illustrates an exploded view of the cap of FIG. 10A.
Figure 11A:
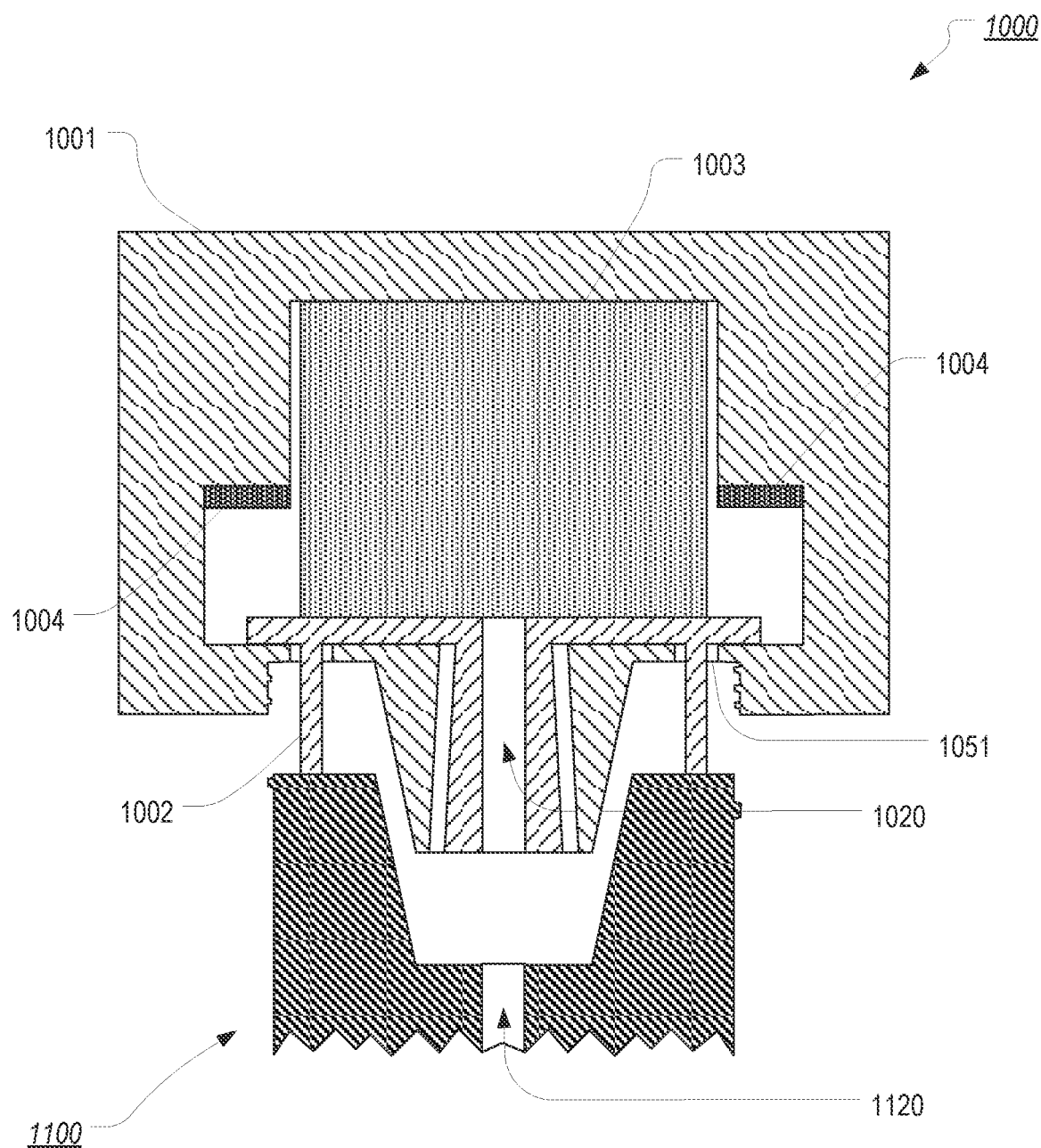
FIGS. 11A-11C illustrate a sequence of how the cap depicted in FIG. 10A is connected to a port of an intravenous device.
Figure 11B:
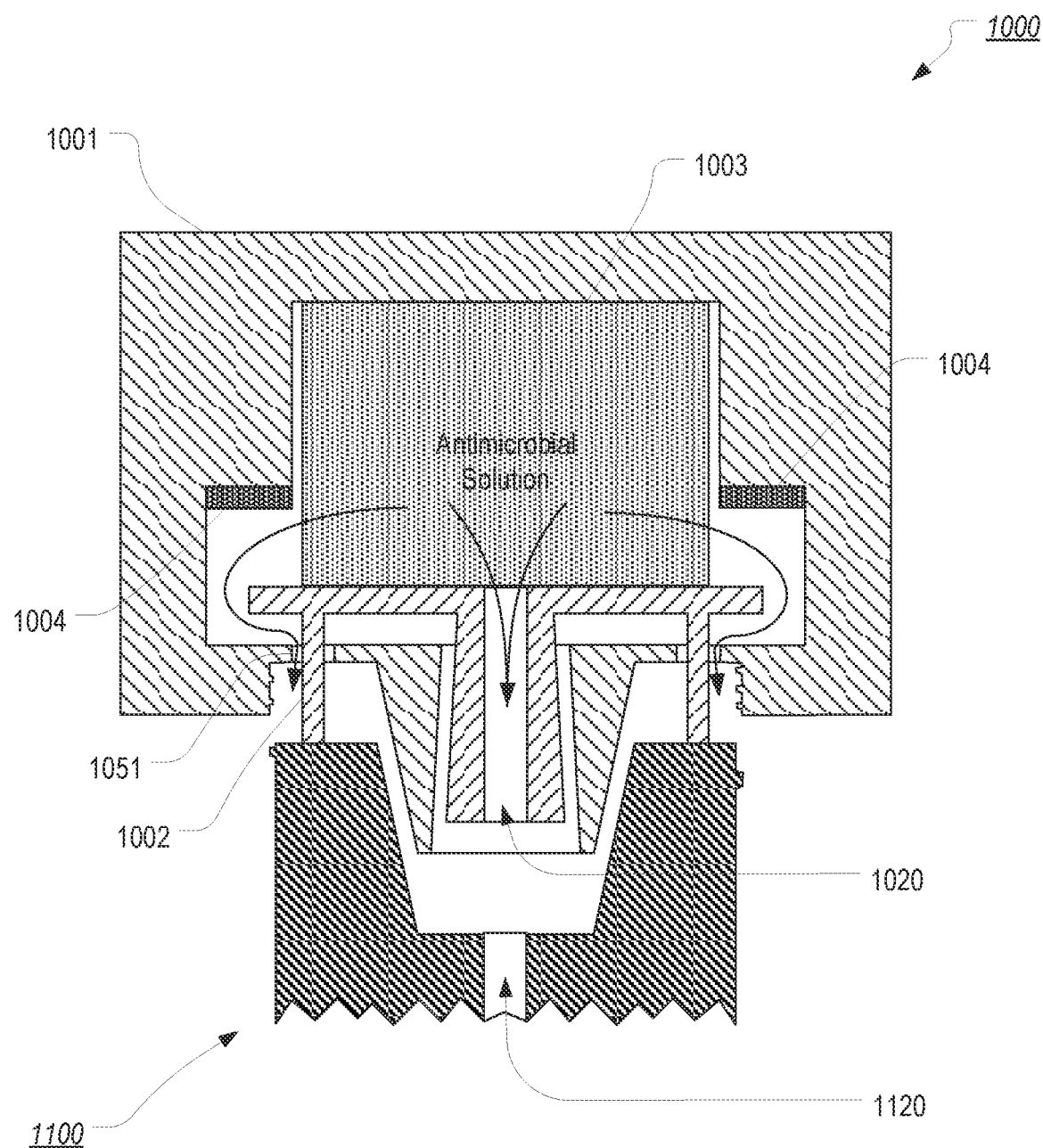
Figure 11C:
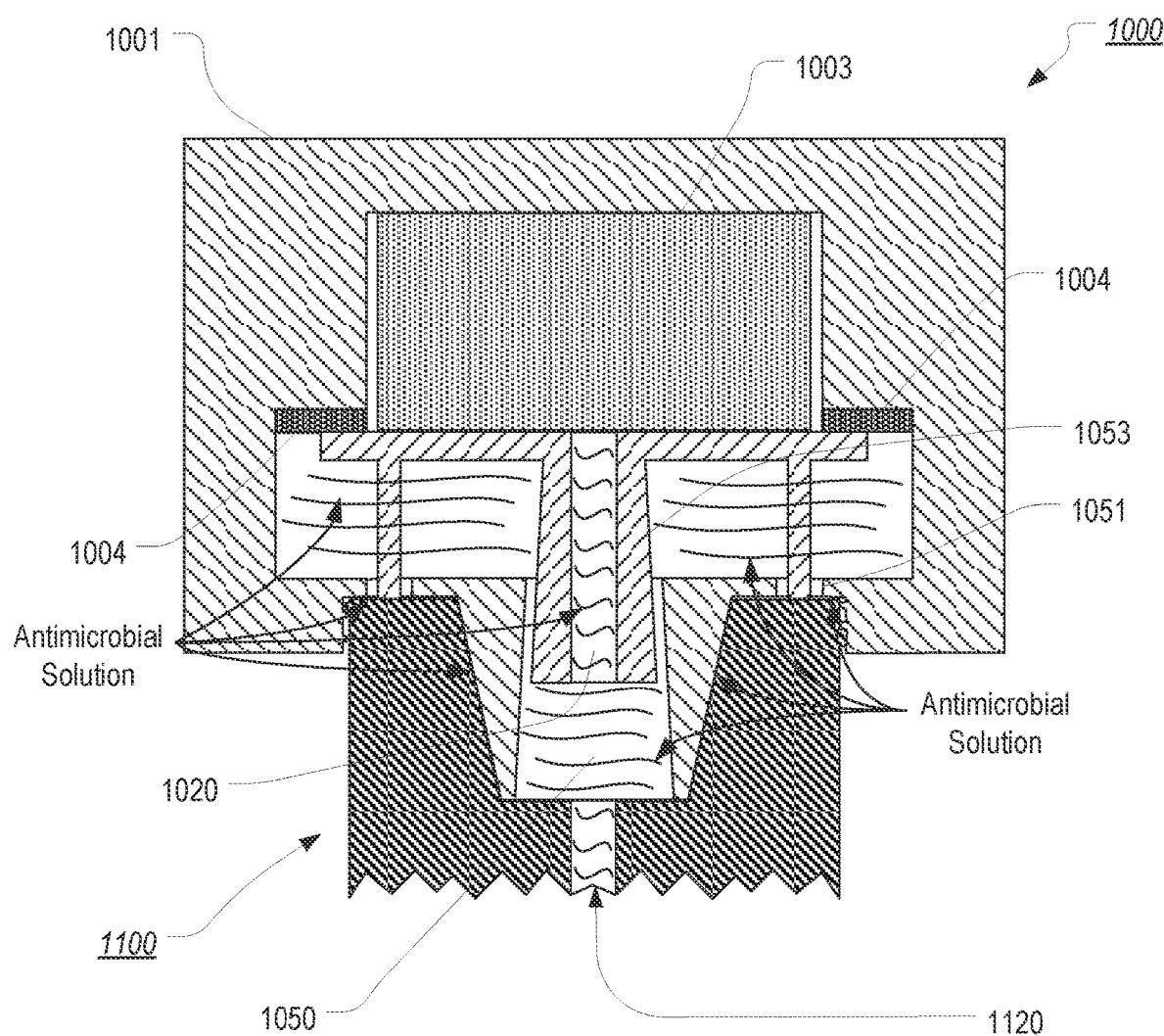

FIG. 10B illustrates a cross-sectional exploded view of cap 1000 in which actuator 1002 is shown removed from body 1001. As shown, actuator 1002 includes a central protrusion 1053 that forms lumen 1020. Actuator 1002 also includes prongs 1052 that extend from the bottom surface of actuator 1002. The bottom of body 1001 is configured to accommodate actuator 1002. For example, body 1001 includes a lumen 1050 within which protrusion 1053 is contained and openings 1051 through which prongs 1052 extend. FIGS. 11A-11C illustrate how this configuration of cap 1000 enhances the flow of antimicrobial solution to the exterior surfaces of a port while still distributing sufficient antimicrobial solution to the lumen of the port.

FIG. 11A illustrates cap 1000 upon actuator 1002 contacted the top surface of port 1100. As shown, the design of actuator 1002 causes prongs 1052 to first contact port 1100. Then, in FIG. 11B, the upward force on prongs 1052 causes actuator 1002 to compress absorbent material 1003 resulting in antimicrobial solution flowing through lumen 1020 and around the exterior of actuator 1002 in much the same manner as described with reference to FIG. 7B.

However, because of the positioning of openings 1051 near the edges of port 1100, the antimicrobial solution that flows through openings 1051 will more easily flow onto the exterior surfaces of port 1100. Additionally, as with cap 300, the primary pathway of the flow of the antimicrobial solution is through lumen 1020 and into lumen 1120 of port 1100.

FIG. 11C illustrates cap 1000 once fully connected to port 1100. As shown, in this position, port 1100 has forced actuator 1002 upward until it contacts seal 1004. At this point, antimicrobial solution will be forced to flow through lumen 1020. However, the antimicrobial solution that flowed around actuator 1002 and is contained within the internal spaces of body 1001 will be allowed to flow out through openings 1051 onto the exterior surfaces of port 1100.

Although FIG. 11C shows that a gap exists between protrusion 1053 and the internal surfaces of lumen 1050 when cap 1000 is fully connected, in some embodiments, the dimensions of protrusion 1053 and lumen 1050 can be configured so that protrusion 1053 forms a tight seal within lumen 1050 when actuator 1002 is in the upward position. Forming a seal between protrusion 1053 and lumen 1050 may be desired when a tight seal is not formed between port 1100 and body 1001.

The caps of the present invention also provide the advantage of minimizing the concentrations of antimicrobial solution that must be used to ensure that the port is adequately disinfected. For example, as stated in the Background, one problem that arises when antimicrobial coatings are used is that the coatings may be too concentrated and may therefore pose toxicity problems. In contrast, because the caps of the present invention are intended for one-time use and are deployed when the port is not in use, the concentrations of antimicrobial solution can be minimized. In other words, in contrast to coatings which must remain active from the time they are applied to the port (e.g. when manufactured) until the port will no longer be used, the caps of the present invention will only remain on the port in between uses. Because the fluid volume in the port is static and fixed, the concentration of the antimicrobial solution will not change when the cap is in place. Therefore a reduced concentration of antimicrobial solution can be employed in the caps of the present invention while still providing adequate antimicrobial protection. In some embodiments, the concentration of the antimicrobial solution (or the concentration once mixed with fluid already present within the lumen of the port) can be just higher than the minimum inhibitory concentration of the antimicrobial agent in the solution.

Many different types of antimicrobial solutions may be used in caps of the present invention. For example, any antimicrobial agent that is soluable in alcohol, saline, or saline/heparin solutions can be employed. The concentration of the antimicrobial agent within the antimicrobial solution can be selected so that the resulting concentration of the agent once the antimicrobial solution is mixed with the fluid in the lumen of the port is above the minimum inhibitory concentration of the antimicrobial agent. Suitable antimicrobial agents include CHA and CHG among others.

In alternate embodiments, the lumen of the actuator can be coated with an antimicrobial coating. In such embodiments, the cap may or may not also include the absorbent material containing the antimicrobial solution. For example, when the cap does not include the absorbent material, the antimicrobial protection can be provided when the fluid within the lumen of the port contacts the antimicrobial coating within the lumen of the actuator. The dry antimicrobial coating can dissolve into the fluid to thereby disinfect the lumen of the port. Providing an antimicrobial coating on the lumen of the actuator as opposed to on the lumen of the port can allow a lower concentration of antimicrobial agent to be used for the reasons described above.

When the cap does include the absorbent material and an antimicrobial coating, the flow of the antimicrobial solution from the absorbent material may be partially or completely directed around the exterior of the actuator to ensure distribution on the exterior surfaces of the port. Some antimicrobial solution may be designed to flow through the lumen in the actuator to assist in distributing the antimicrobial coating throughout the lumen of the port. In this way, an antimicrobial solution can still be directed to both the intraluminal and the exterior surfaces of the port.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A cap for a port of an intravenous device, the cap comprising:
 a body having a cavity;
 an actuator positioned within the cavity, the actuator having a first opening, a second opening, and a lumen extending therebetween, the lumen configured to allow fluid to freely flow between the first opening and the second opening; and
 an absorbent material containing an antimicrobial solution, the absorbent material being positioned within the body such that the absorbent material is compressible,
 wherein when the cap is connected to a port of an intravenous device, the actuator compresses the absorbent material causing the antimicrobial solution to automatically flow through the lumen of the actuator and into the port.

2. The cap of claim 1, wherein the actuator comprises a male luer in which the lumen is formed.

3. The cap of claim 1, wherein the antimicrobial solution flows through a gap between the body and an exterior surface of the actuator and onto an exterior surface of the port.

4. The cap of claim 1, wherein the body includes a seal that the actuator contacts when the cap is connected to the port thereby forming a seal between the actuator and the body.

5. The cap of claim 1, wherein the actuator includes a protrusion that is positioned within a lumen in the body, the protrusion having a lumen through which the antimicrobial solution flows.

6. The cap of claim 1, wherein the lumen includes an antimicrobial coating.

7. The cap of claim 5, wherein the actuator includes a plurality of prongs that extend through corresponding openings in the body.

8. The cap of claim 7, wherein the antimicrobial solution flows through the corresponding openings when the actuator is forced into the cavity.

9. A method for cleaning a port of an intravenous device, the method comprising:
 connecting a cap to a port of an intravenous device, wherein the cap comprises:
 a body having a cavity;
 an actuator positioned within the cavity, the actuator having a first opening, a second opening, and a lumen extending therebetween, the lumen configured to allow fluid to freely flow between the first opening and the second opening; and
 an absorbent material containing an antimicrobial solution, the absorbent material being positioned within the body such that the absorbent material is compressible,
 wherein when the cap is connected to a port of an intravenous device, the actuator compresses the absorbent material causing the antimicrobial solution to automatically flow through the lumen of the actuator and into the port.

10. The method of claim 9, wherein the actuator comprises a male luer in which the lumen is formed.

11. The method of claim 9, wherein the antimicrobial solution flows through a gap between the body and an exterior surface of the actuator and onto an exterior surface of the port.

12. The method of claim 9, wherein the body includes a seal that the actuator contacts when the cap is connected to the port thereby forming a seal between the actuator and the body.

13. The method of claim 9, wherein the actuator includes a protrusion that is positioned within a lumen in the body, the protrusion having a lumen through which the antimicrobial solution flows.

14. The method of claim 9, wherein the lumen includes an antimicrobial coating.

15. The method of claim 13, wherein the actuator includes a plurality of prongs that extend through a plurality of openings in the body.

16. The method of claim 15, wherein the antimicrobial solution flows through the plurality of openings in the body when the actuator is forced into the cavity.

* * * * *